(12) United States Patent
Kauphusman et al.

(10) Patent No.: US 7,824,377 B2
(45) Date of Patent: Nov. 2, 2010

(54) TISSUE ANCHORING CATHETER SYSTEMS AND METHODS

(75) Inventors: James V. Kauphusman, Champlin, MN (US); Israel A. Byrd, Richfield, MN (US); Saurav Paul, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 11/962,512

(22) Filed: Dec. 21, 2007

(65) Prior Publication Data

US 2009/0163862 A1    Jun. 25, 2009

(51) Int. Cl.
*A61M 5/178* (2006.01)

(52) U.S. Cl. ............ 604/164.04; 604/117; 604/164.01; 604/164.09; 604/164.11; 604/523

(58) Field of Classification Search ........... 04/158–163, 04/137, 164.08–164.11, 173; 604/106–107, 604/158–163, 137, 168.08–164.11, 173, 604/264, 272, 164.04
See application file for complete search history.

(56) References Cited

U.S. PATENT DOCUMENTS

| | | | |
|---|---|---|---|
| 4,222,380 A * | 9/1980 | Terayama | 604/115 |
| 4,799,495 A * | 1/1989 | Hawkins et al. | 600/567 |
| 4,898,577 A | 2/1990 | Badger et al. | |
| 5,030,204 A | 7/1991 | Badger et al. | |
| 5,228,441 A | 7/1993 | Lundquist | |
| 5,243,167 A | 9/1993 | Lundquist et al. | |
| 5,315,996 A | 5/1994 | Lundquist | |
| 5,322,064 A | 6/1994 | Lundquist | |
| 5,329,923 A | 7/1994 | Lundquist | |
| 5,334,145 A | 8/1994 | Lundquist | |
| 5,354,279 A * | 10/1994 | Hofling | 604/164.12 |

(Continued)

FOREIGN PATENT DOCUMENTS

EP    0361314 A2    4/1990

(Continued)

OTHER PUBLICATIONS

Biocardia, "MORPH Universal Deflectable Guide Catheter," available at www.biocardia.com/img/Morph-Full-Pg-Brochure-Final.jpg at least as early as Sep. 12, 2006; 1 page.

(Continued)

*Primary Examiner*—Nicholas D Lucchesi
*Assistant Examiner*—Leah Stohr
(74) *Attorney, Agent, or Firm*—Trenner Law Firm LLC (57) ABSTRACT

Catheter systems and methods are disclosed for anchoring the catheter system to tissue, e.g., for delivery of biologic or chemical agents, or other therapeutic fluid during various procedures. An exemplary tissue anchoring catheter comprises an outer catheter shaft connected to a catheter handle. A delivery sheath is provided within the outer catheter shaft, the delivery sheath housing a needle. At least one anchor is operatively associated with the delivery sheath, the at least one anchor operable at the catheter handle to secure the delivery sheath to tissue for conveying biologic or chemical agents, or other therapeutic fluid from the needle to the tissue. The tissue anchoring catheter may further comprise sensing means such as piezoelectric, pressure, thermistor, thermocouple, or ultrasound sensors.

30 Claims, 11 Drawing Sheets

U.S. PATENT DOCUMENTS

| | | | |
|---|---|---|---|
| 5,405,376 | A | 4/1995 | Mulier et al. |
| 5,419,777 | A * | 5/1995 | Hofling .................. 604/264 |
| 5,454,787 | A | 10/1995 | Lundquist |
| 5,477,856 | A | 12/1995 | Lundquist |
| 5,643,255 | A * | 7/1997 | Organ .................... 606/41 |
| 5,685,868 | A | 11/1997 | Lundquist |
| 6,554,794 | B1 | 4/2003 | Mueller et al. |
| 6,626,902 | B1 | 9/2003 | Kucharczyk et al. |
| 2004/0260240 | A1 | 12/2004 | Beyerlein |
| 2006/0264950 | A1 | 11/2006 | Nelson et al. |

FOREIGN PATENT DOCUMENTS

| | | |
|---|---|---|
| EP | 0521595 A2 | 7/1993 |
| JP | 2-193681 | 7/1990 |
| JP | 7-255855 | 10/1995 |

OTHER PUBLICATIONS

Biocardia, "Products and Services—Helical Infusion Catheter," available at www.biocardia.com/products/helical.htm at least as early as Sep. 12, 2006; copyright 2004; 1 page.

Fotinos, et al., "Invited Review: 5-Aminolevulnic Acid Derivatives in Photomedicine: Charcteristics, Application and Perspectives," Photochemistry and Photobiology, 2006, pp. 994-1015.

Damiano, et al., "The effect of chemical ablation of the endocardium on ventricular fibrillation threshold," Circulation Journal of the American Heart Association, 1986, pp. 645-652.

Brugada, et al., "Transcoronary Chemical Ablation of Ventricular Tachycardia," Department of Cardiology, University of Limburg, Academic Hospital, Maastrict, The Netherlands, 1988, pp. 475-482.

PCT International Search Report and Written Opinion of the International Searching Authority for PCT/US08/085261, dated Feb. 4, 2009, 9 pages.

* cited by examiner

TISSUE ANCHORING CATHETER SYSTEMS AND METHODS

BACKGROUND OF THE INVENTION a. Field of the Invention

The instant invention is directed toward catheter systems and methods for anchoring the catheter in tissue, e.g., for delivery of a biologic or chemical agent, or other therapeutic fluid. In particular, the catheter of the present invention comprises anchoring means which may be used to anchor the catheter system to the tissue, fluid delivery means for delivery of a biologic or chemical agent, or other therapeutic fluid to the tissue, and means for tissue contact assessment during these procedures.

b. Background Art

Normal heart rhythm is between 60 and 100 beats per minute. Tachycardia is a fast heart rate (usually over 100 beats per minute) caused by disease or injury. Tachycardias may begin in the upper chambers of the heart (the atria) or the lower chambers of the heart (the ventricles). Some tachycardias are harmless, but other tachycardias are life threatening. Tachycardias can deteriorate to fibrillation, a disorder in which, the heart does not move enough blood to meet the needs of the body.

Atrial fibrillation (AF) is the most common abnormal heart rhythm. It is a very fast, uncontrolled heart rhythm that occurs when the upper chambers of the heart (the atria) try to beat so fast between 350 and 600 times per minute) that they only quiver. Ventricular fibrillation (VF) occurs when the lower chambers of the heart (the ventricles) produce fast and erratic electrical impulses that fail to induce synchronous mechanical contraction, such that oxygenated blood is not circulated through the body. Fibrillation in the ventricles is a life-threatening arrhythmia demanding immediate treatment.

Before a tachycardia deteriorates to fibrillation, various procedures may be used to treat the heart tissue and reduce or altogether eliminate the occurrence of fibrillations. It is well known that treatment benefits may be gained by delivering biologic or chemical agents, or other therapeutic fluid to heart tissue if the depth and location of delivery can be controlled. For example, chemical agents may be used to create lesions in tissue, which change the electrical properties of the tissue. For example, when lesions are formed at specific locations in cardiac tissue, undesirable atrial fibrillations may be lessened or eliminated. Likewise, biologic and chemical agents may be delivered into infracted tissue in the lower chambers of the heart (the ventricles) to promote angiogenesis for the treatment of Ventricular Tachycardia (VT). Other procedures are also known for treating these and other ailments. Use of particular biologic or chemical agents, or other therapeutic fluid depends at least to some extent on the procedure, desired treatment. and may also depend on other considerations, such as tissue characteristics.

Several difficulties may be encountered, however, when attempting to deliver biologic or chemical agents, or other therapeutic fluid at specific locations in the tissue using some existing catheters. For example, establishing and maintaining adequate tissue contact during the procedure is not always readily achieved. Typically, the physician determines tissue contact based on his/her experience maneuvering the catheter. Such experience only comes with time, and may be quickly lost if the physician does not perform the procedure on a regular basis. When used inside the heart, the beating heart further complicates matters by making it difficult to establish and maintain sufficient contact with the tissue for a sufficient length of time to deliver the desired dose of biologic or chemical agents, or other therapeutic fluid. If the contact with the tissue cannot be properly maintained during the procedure, the procedure may be unsuccessful and may need to be repeated. In ablation procedures, for example, the amount of contact is critical to form sufficiently deep ablative lesions on the tissue without damaging surrounding tissue in the heart.

Thus, there remains a need for establishing and maintaining tissue contact during a procedure for delivery of biologic or chemical agents, or other therapeutic fluid.

BRIEF SUMMARY OF THE INVENTION

It is desirable to be able to establish and maintain adequate contact with tissue for delivery of biologic or chemical agents, or other therapeutic fluid during various procedures. This can be accomplished by anchoring a portion of the catheter system to the tissue for delivery of biologic or chemical agents, or other therapeutic fluid during various procedures.

The present invention may be implemented in a catheter system that anchors to tissue during a medical procedure (e.g., biologic treatment of VT or chemical ablation procedures) for delivery of biologic or chemical agents, or other therapeutic fluid. In an exemplary embodiment, one or more anchoring means is operatively associated the distal portion of the catheter system. Once positioned, the anchoring means enables a physician (or other user) to maintain the position and desired level of contact with a moving tissue for delivery of biologic or chemical agents, or other therapeutic fluid during the procedure.

The present invention includes tissue anchoring catheters. In an exemplary embodiment, a tissue anchoring catheter comprises an outer catheter shaft connected to a catheter handle. A delivery sheath is provided within the outer catheter shaft, and the delivery sheath houses a needle. At least one anchor is operatively associated with the delivery sheath. The at least one anchor is operable at the catheter handle to secure the delivery sheath to tissue for conveying a fluid from the needle to the tissue.

The present invention also includes a system comprising means for guiding a delivery sheath adjacent tissue. The system also comprises means for anchoring the delivery sheath to the tissue. The system also comprises means for deploying a needle from within the delivery sheath for conveying a therapeutic fluid from the needle to the tissue.

The present invention also includes methods of anchoring catheters. In an exemplary embodiment, a method comprises: guiding a delivery sheath adjacent tissue, anchoring the delivery sheath to the tissue, deploying a needle from within the delivery sheath, and conveying a therapeutic fluid from the needle to the tissue.

In an exemplary embodiment, the anchor is a helical or spiral fixation needle. The inner diameter of the catheter system is capable of supporting a spiral tipped fixation needle. The helical needle is turned from the proximal end via a knob on the catheter handle which pulls the distal portion of the catheter into the endocardial surface similar to a corkscrew. This attachment allows the catheter system to be precisely positioned in an area of infarction and helps maintain its position. Through the center of the spiral fixation device, an injection needle (e.g., 25 gauge needle) is passed and pushed into the target tissue. The catheter may also be used epicardially (e.g., from treatment of VT). In exemplary embodiments, a preferentially directed needle may be injected into the epicardial tissue near the infarction for delivery of a therapeutic fluid. The helical needle may itself include at least one fluid delivery port, making the separate needle optional.

In another embodiment, the anchor includes at least one barb. The barb may deploy automatically as the needle advances out of the delivery sheath. The barb may also retract automatically as the needle is pulled back into the delivery sheath.

In any event, the needle is capable of delivering biologic or chemical agents, or other therapeutic fluid to the tissue over a time frame considered adequate by the physician without concern that the catheter will move from its position.

The catheter system may also be implemented for tissue contact assessment. For example, the catheter system may also comprise sensing means (e.g., piezoelectric, pressure, thermistor, thermocouple, or ultrasound sensors) for assessing tissue contact. In exemplary embodiments, the catheter system may include one or more electrodes for electrogram mapping of heart tissue (e.g., for use endocardially for treatment of VT). Feedback may be conveyed to the user in real-time (e.g., at a display device or other interface) so that the user can properly position the catheter system adjacent the target tissue and anchor the catheter system in place for the procedure.

Feedback may also enable the user to assess depth of the needle within the tissue. A needle deployment system may be implemented to control needle depth near the catheter handle. The needle deployment system may include an adjustable depth control ring and a plunger. The needle deployment system ejects the needle from the delivery sheath as the plunger is moved toward the depth control ring, and the depth control ring stops movement of the plunger at a preset depth. The plunger may be spring-biased to automatically retract the needle within the delivery sheath when the plunger is released.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 2b is a cross-sectional view of the tip portion of the sheath shown in FIG. 2a.

DETAILED DESCRIPTION OF THE INVENTION

Several embodiments of a catheter system according to the present invention are depicted in the figures as the catheter system may be anchored to tissue for delivery of biologic or chemical agents, or other therapeutic fluid during a medical procedure. As described further below, the catheter of the present invention provides a number of advantages, including, for example, the ability to control and maintain tissue contact for delivery of biologic or chemical agents, or other therapeutic fluid (e.g., for lesion formation in tissue). The catheter system facilitates more reliable delivery of biologic or chemical agents, or other therapeutic fluid, than other devices. The catheter system also facilitates delivery of biologic or chemical agents, or other therapeutic fluid in difficult environments (e.g., to the tissue of a beating heart).

Before continuing, it is noted that other components typical of systems which are conventionally implemented for such procedures, are not shown or described herein for purposes of brevity. Such components may nevertheless also be provided as part of, or for use with, the catheter. For example, catheter systems commonly include or are used in conjunction with an ECG recording system, and/or various input and output devices. Such components are well understood in the medical devices arts and therefore further explanation is not necessary for a complete understanding of the invention.

Figure 1:
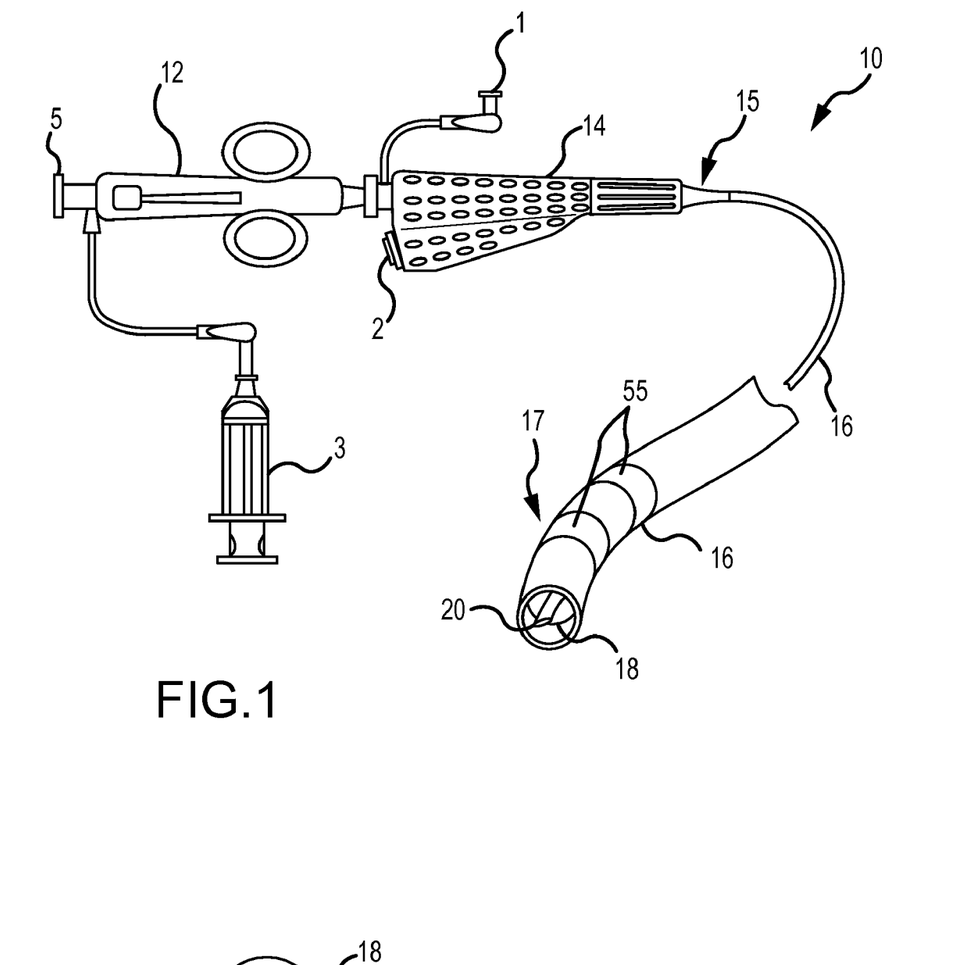
FIG. 1 is a perspective view of an exemplary embodiment of a catheter system which may implement anchoring means.

FIG. 1 is a perspective view of an exemplary embodiment of a catheter system 10 which may implement anchoring means (such as the anchoring means shown in FIG. 4a-c, FIG. 5a-c, and FIG. 8). The catheter system 10 may include a handle 12 and connector 14 at the base or proximal end 15. An outer catheter shaft also referred to as a "guiding introducer" 16 having a tubular body is connected to the connector 14 on the proximal end (e.g., illustrated by reference number 15 in FIG. 1) of the catheter system 10. As used herein and commonly used in the art, the term "proximal" is used generally to refer to components or portions of the catheter system 10, such as the handle 12 and connector 14 that are located or generally orientated away from or opposite the heart or other target tissue when the catheter system 10 is in use. On the other hand, the term "distal" (e.g., illustrated in FIG. 1 by reference number 17) is used generally to refer to components located or generally orientated toward the heart or other target tissue when the catheter system 10 is in use.

The guiding introducer 16 defines at least one lumen or longitudinal channel. A delivery sheath 18 is fitted through the guiding introducer 16. In one implementation, the guiding introducer 16 and sheath 18 are fabricated from a flexible resilient material, and are preferably fabricated of materials suitable for use in humans, such as nonconductive polymers. Suitable polymers include those well known in the art, such as polyurethanes, polyether-block amides, polyolefins, nylons, polytetrafluoroethylene, polyvinylidene fluoride, and fluorinated ethylene propylene polymers, and other conventional materials. Some portions of the guiding introducer 16 and/or sheath 18 may be braided for enhanced stiffness.

In exemplary implementations, the guiding introducer 16 and sheath 18 are each about two to four feet long, so that they may extend from the left atrium through the body and out of the femoral vein in the right leg and be connected with various catheter devices such as the connector 14, one or more fluid control valves 1-3, and the like.

Figure 2A:
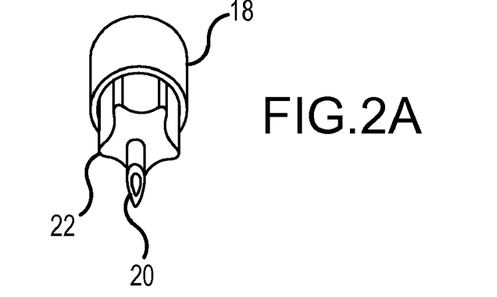
FIG. 2a is a perspective view of a tip portion of a sheath showing an exemplary embodiment of a support structure providing mechanical support for a needle within a shaft of the sheath.
Figure 2B:
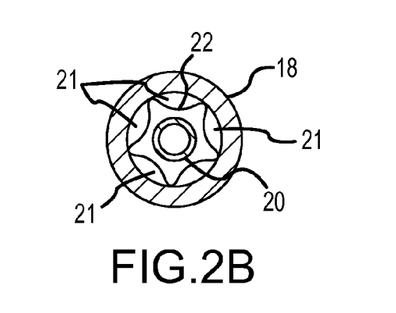
Figure 2C:
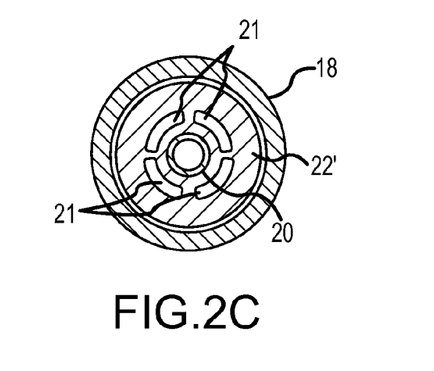
FIG. 2c is a cross-sectional view of another exemplary embodiment of a support structure providing mechanical support for the needle within a shaft of the sheath.

The sheath 18 is configured to receive and guide a needle 20 within the lumen to the target tissue. FIG. 2*a* is a perspective view of a tip portion of the sheath 18 showing an exemplary embodiment of a support structure 22 providing mechanical support for the needle 20 within a shaft of the sheath 18. FIG. 2*b* is a cross-sectional view of the tip portion of the sheath 18 shown in FIG. 2*a*. In this embodiment, the support structure 22 is substantially star-shaped and maintains the needle 20 approximately in the center of the sheath 18. FIG. 2*c* is a cross-sectional view of another exemplary embodiment of a support structure 22' providing mechanical support for the needle 20 within a shaft of the sheath 18. In this embodiment, the support structure 22' is substantially radial-shaped. This embodiment also maintains the needle 20 approximately in the center of the sheath 18.

Although not required, the support structure 22 may include one or more interstitial spaces (e.g., spaces 21 formed between the support structure 22 and the sheath 18 as shown in FIG. 2*b*-*c*). These interstitial spaces may be used to inject fluids around the needle (e.g., flushing fluids, dyes, etc.).

Although the sheath 18 is depicted as having a circular cross-section, it is noted that the sheath 18 may intentionally or unintentionally have a wide variety of cross-sectional configurations and areas, and need not be circular. For example, manufacturing irregularities may result in the sheath 18 having different cross-sectional configurations. Or for example, the sheath 18 may be intentionally selected to have different cross-sectional configurations to achieve desired properties.

Of course other designs of the support structure may also be implemented as will be readily understood by those having ordinary skill in the art after becoming familiar with the teachings herein. It is noted that the support structure need not maintain the needle in the center of the sheath. It is only desired that the needle be maintained in a substantially constant position within the diameter of the sheath so that the physician (or other operator) will be better able to control positioning of the needle during the procedure.

The particular types and configuration of support structure used will depend at least to some extent on design considerations. Exemplary design considerations may include, but are not limited to, the material and desired structural properties, the length, shape, and cross-sectional area of the sheath. And of course, the design parameters may be different for various procedures or physician preferences.

The sheath 18 is pre-positioned in the appropriate location in the heart prior to inserting the needle 20. To pre-position the sheath 18 at the appropriate location in the heart, a dilator (not shown) is first fitted through the sheath 18. In an example of a procedure within the left atrium, the sheath 18 and the dilator are first inserted in the femoral vein in the right leg. The sheath and dilator are then maneuvered up to the inferior vena cava and into the right atrium. In what is typically referred to as a transseptal approach, the dilator is pressed through the interatrial septum between the right and left atria. A dilator needle may be used here to make an opening for the dilator to pass through. This dilator needle is typically different from the needle 20 used for the procedure. The dilator expands the opening sufficiently so that the sheath 18 may then be pressed through the opening to gain access to the left atrium and the pulmonary veins. With the sheath 18 in position, the dilator is removed and the needle 20 is fed into the lumen of the sheath 18 and pushed along the sheath 18 into the left atrium. When positioned in the left atrium, various procedures, such as those described above, may be performed within the heart tissue.

Before continuing, it is noted that the catheter system 10 has been described as it may be inserted for procedures in the left atrium in the vicinity of or within the pulmonary veins of the heart. The catheter system 10, however, is not limited to such procedures, and may be used for procedures involving other target tissue in other areas of the heart and body.

Figure 3:
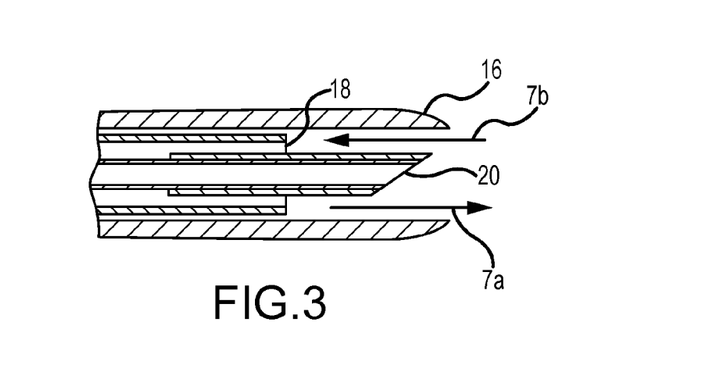
FIG. 3 is a cross-sectional view of a tip portion of a catheter system showing an exemplary needle for delivery of biologic or chemical agents, or other therapeutic fluid.

Once the sheath 18 is pre-positioned in the appropriate location in the heart, the needle 20 may be at least partially extended out from the lumen at the distal end 17 of the sheath 18 (e.g., in the direction illustrated by arrow 7*a* in FIG. 3) so that the needle 20 may be inserted into the target tissue for delivery of a biologic or chemical agent or other therapeutic fluid. The needle 20 may also be retracted (e.g., in the direction of arrow 7*b*) before removing the catheter system 10 from the body.

Figure 4A:
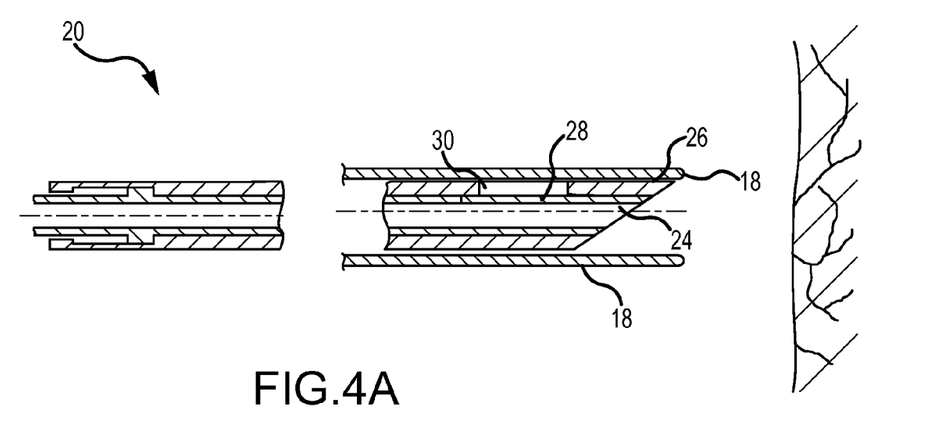
FIG. 4a-d are cross-sectional views of a needle showing an exemplary embodiment of an anchor for securing the catheter system to a tissue, wherein (a) shows the anchor in a closed position as it may be inserted into the tissue, (b) shows the anchor in an engaging position within the tissue, (c) shows the anchor as it may be returned to a closed position within the tissue, and (d) shows the needle as it may be withdrawn from the tissue.
Figure 4B:
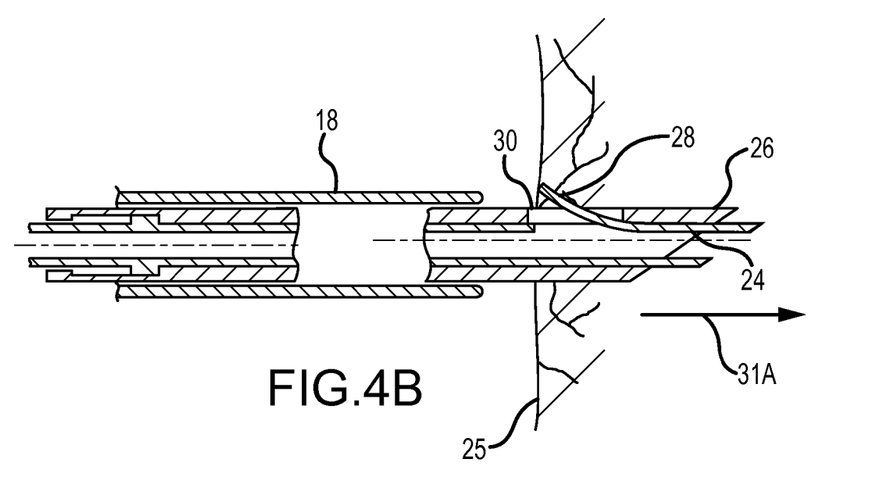
Figure 4C:
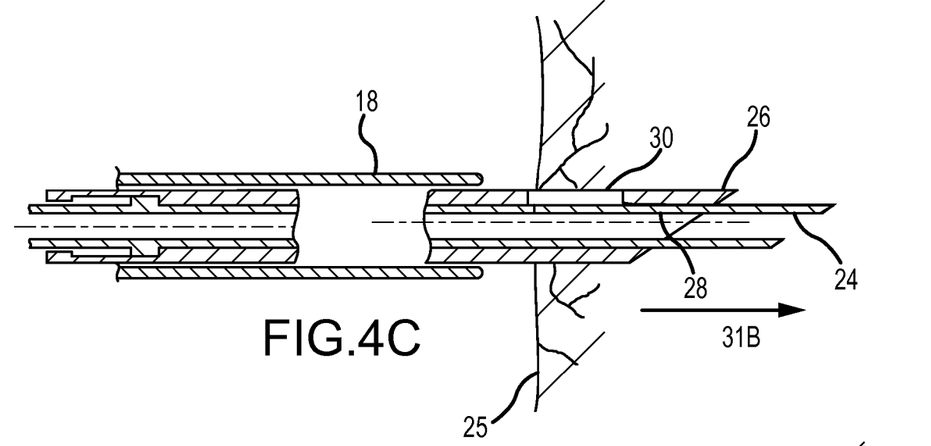

FIG. 4*a*-*c* is a cross-sectional view of a needle 20 showing an exemplary embodiment of an anchor for securing the needle 20 to tissue 25. In this embodiment, the needle 20 includes an inner portion 24 and an outer portion 26. The anchor is implemented as one or more barbs (one barb 28 is shown) on the inner portion 24 of the needle 20. An opening or window 30 is formed through the outer portion 26 of the needle 20. During use, the needle 20 is advanced (e.g., in the direction illustrated by arrow 31*a* in FIG. 4*b*) so that it extends beyond the sheath 18 and can be inserted into the tissue 25. The inner portion 24 of the needle 20 may then be further advanced within the tissue 25 (again in the direction illustrated by arrow 31*a*). As the inner portion 24 of the needle 20 advances adjacent the window 30, the barb 28 is automatically deployed (e.g., by a spring-like action) so that the barb 28 extends through the window 30 and engages the tissue 25 as can be seen in FIG. 4*b*. Accordingly, the barb 28 secures the needle 20 to the tissue 25 for delivery of biologic or chemical agents, or other therapeutic fluid.

Figure 4D:
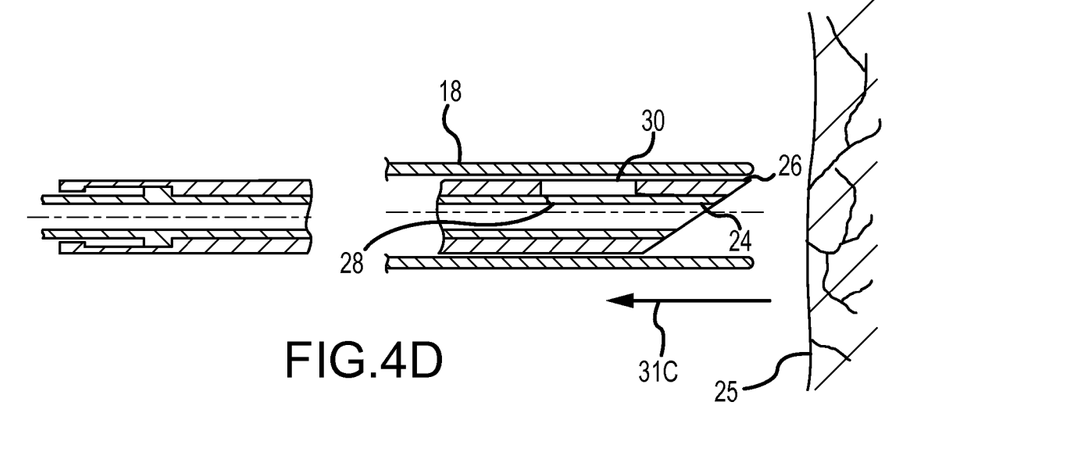

After delivery of the biologic or chemical agents, or other therapeutic fluid, the inner portion 24 of the needle 20 may be further advanced into the tissue 25 (in the direction illustrated by arrow 31*b* in FIG. 4*c*). As the inner portion 24 of the needle 20 advances, the barb 28 passes the opening of window 30 and retracts inside the inner portion 24 of the needle 20 so that the barb 28 is in a closed position. The needle 20 can then be retracted into the sheath 18 and removed from the tissue 25 (in the direction illustrated by arrow 31*c* in FIG. 4*d*). It is noted that the inner portion 24 of the needle 20 is withdrawn together with the outer portion 26 of the needle 20 in such a manner so as not to redeploy the anchor 28 during removal.

Figure 5A:
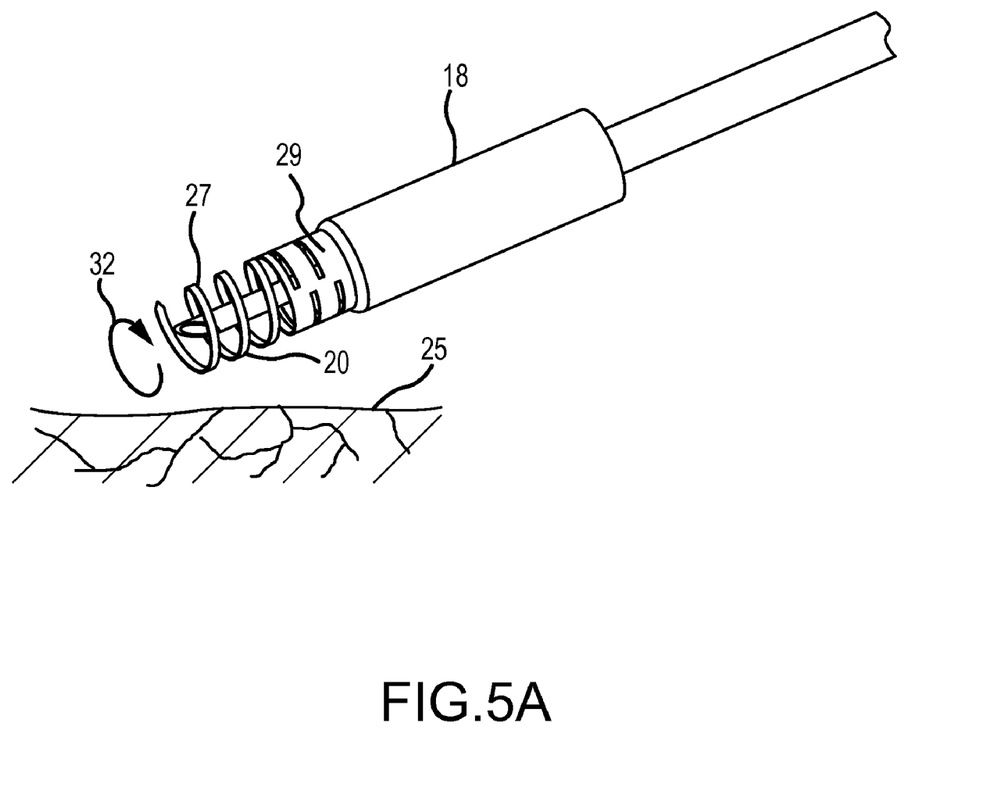
FIG. 5a-c are perspective views of a tip portion of a sheath showing another exemplary embodiment of an anchor for securing the catheter system to a tissue, wherein (a) shows the anchor adjacent tissue, (b) shows the anchor embedded in the tissue, and (c) shows the needle injected into the tissue.
Figure 5B:
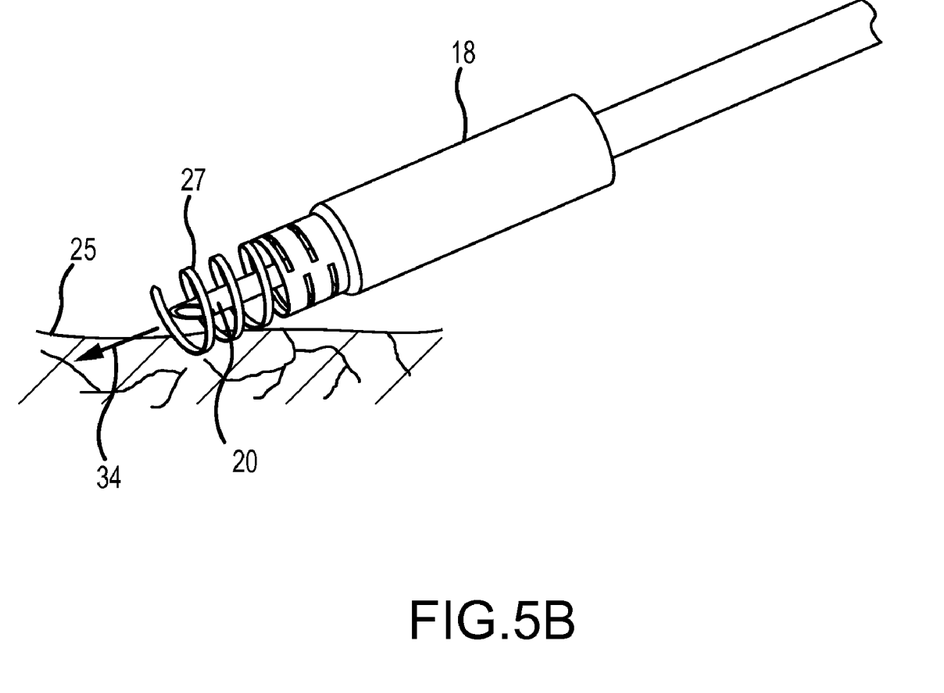
Figure 5C:
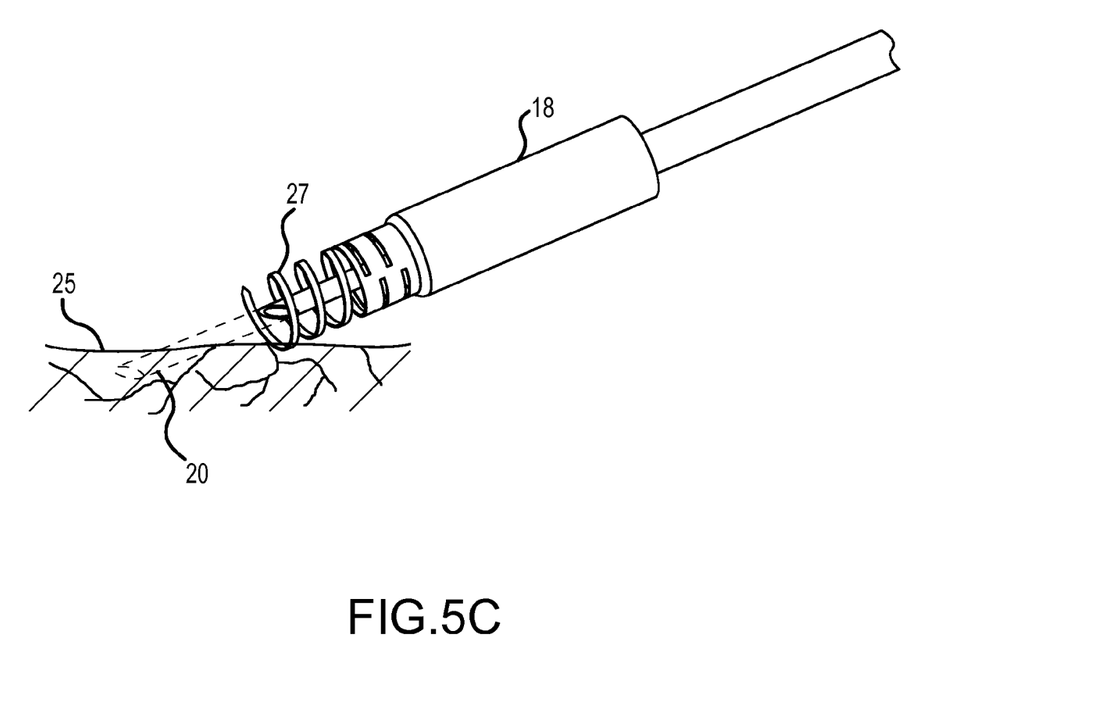

FIG. 5*a*-*c* are perspective views of a tip portion of the sheath 18 (e.g., near distal end 17 as it relates to the catheter system 10 shown in FIG. 1) showing another exemplary embodiment of an anchor for securing the sheath 18 to a tissue 25. In this embodiment, the anchor comprises a helical shaped needle 27. The anchor may be formed as part of the sheath 18 itself. For example, the sheath 18 may include tubing made from metal or other stiff material, which is cut (e.g., by laser) to form a flexible base portion 29 and a helical needle portion 27. In another example, the helical needle portion 27 may be manufactured separately and attached to the sheath 18.

During use, the guiding introducer (refer to FIG. 1 and description thereof, not shown in FIG. 5*a*-*c* for purposes of clarity) may be positioned adjacent the tissue 25 and the sheath 18 advanced so that the sheath 18 extends beyond the guiding introducer 16. The sheath 18 can then be rotated (e.g., in the direction illustrated by arrow 32 in FIG. 5a) so that the helical needle 27 engages the tissue 25 and secures itself to the tissue 25 as shown in FIG. 5b. The needle 20 may then be advanced from within the sheath 18 (e.g., as illustrated by arrow 34 in FIG. 5b) and into the tissue 25 as shown in FIG. 5c for delivery of biologic or chemical agents, or other therapeutic fluid. The needle 20 may be withdrawn following delivery of the biologic or chemical agents, or other therapeutic fluid, and then the helical needle 27 may be removed by rotating it in a direction opposite to that used to engage the helical needle 27. The catheter system 10 may then be withdrawn from the patient's body in a conventional manner.

Figure 6:
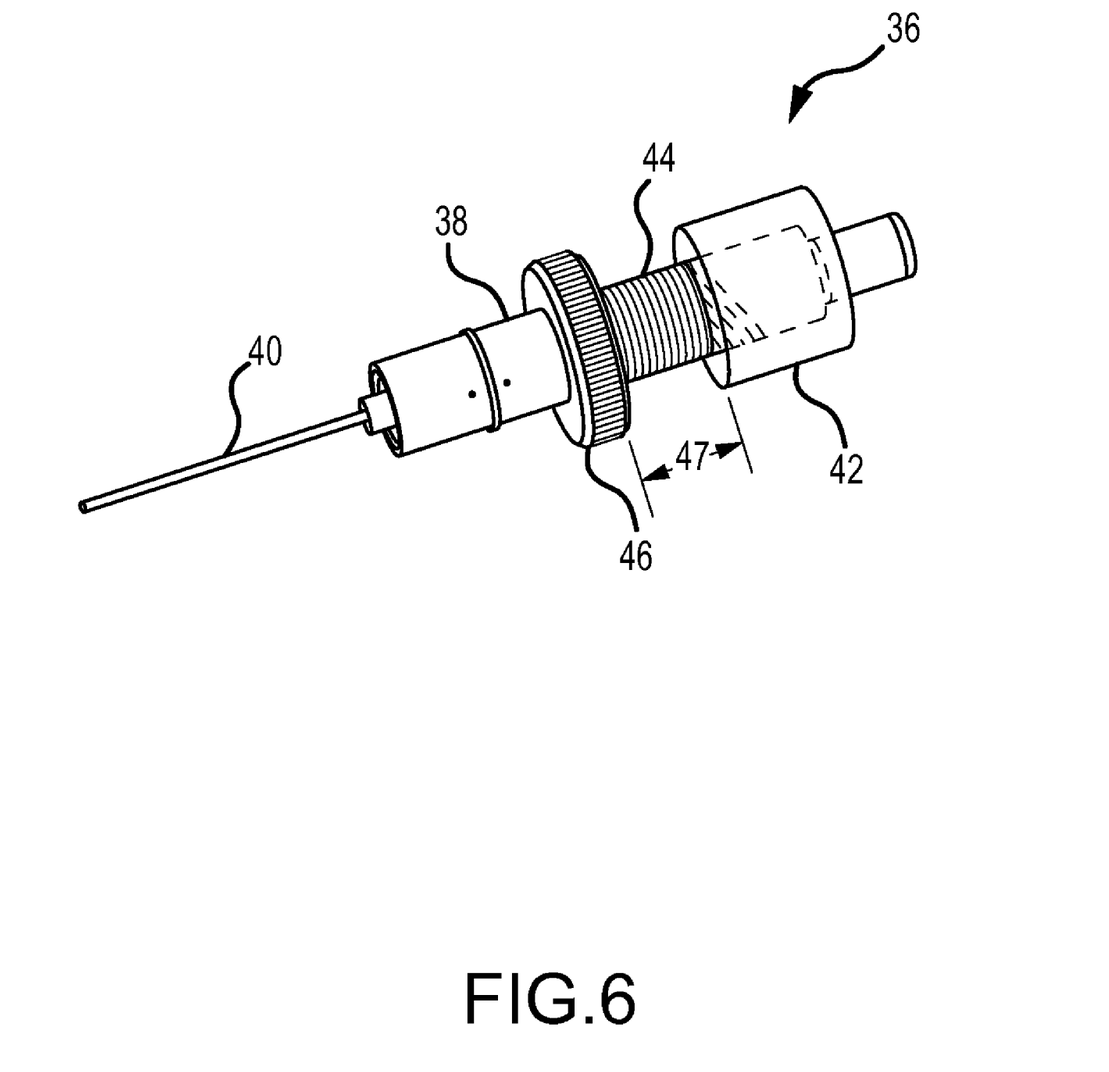
FIG. 6 is a perspective view of a needle deployment system which may be implemented to control insertion of the needle as illustrated in FIG. 5b-c.

FIG. 6 is a perspective view of a needle deployment system 36 which may be implemented to control insertion of the needle 20 to the desired depth within the tissue (e.g., as illustrated by insertion of needle 20 into tissue 25 in FIG. 4b-c or FIG. 5b-c). The needle deployment system 36 may be connected to any of a wide variety of catheter systems (e.g., to port 5 on the handle 12 of catheter system 10 shown in FIG. 1). The needle deployment system 36 includes a handle portion 38 operatively associated with the needle 20 via needle catheter 40. In particular, the needle catheter 40 is connected to a plunger 42 in such a manner that movement of the plunger 42 is directly translated into movement of the needle 20. Hence, the needle 20 moves out from the sheath 18 when the plunger 42 is depressed, and the needle 20 moves back into the sheath 18 when the plunger 42 is automatically retracted or otherwise pulled back toward its starting position.

The needle deployment system 36 may also include a depth control ring 46. In use, the plunger 42 may be pushed or otherwise moved toward the depth control ring 46 (thereby also moving the needle 20) until the plunger 42 abuts against the depth control ring 46. The depth control ring 46 prevents the plunger 42 (and hence the needle 20) from moving more than a predetermined distance. The predetermined distance is illustrated by arrow 47 and is defined as the distance between the plunger 42 in a fully extended or pulled-back position, and the inner surface of the depth control ring 46. The position of depth control ring 46 on the handle portion 38 may be adjusted by turning the depth control ring 46 on the threads 44 to control or set different predetermined distances 47 that the needle can travel.

Figure 7A:
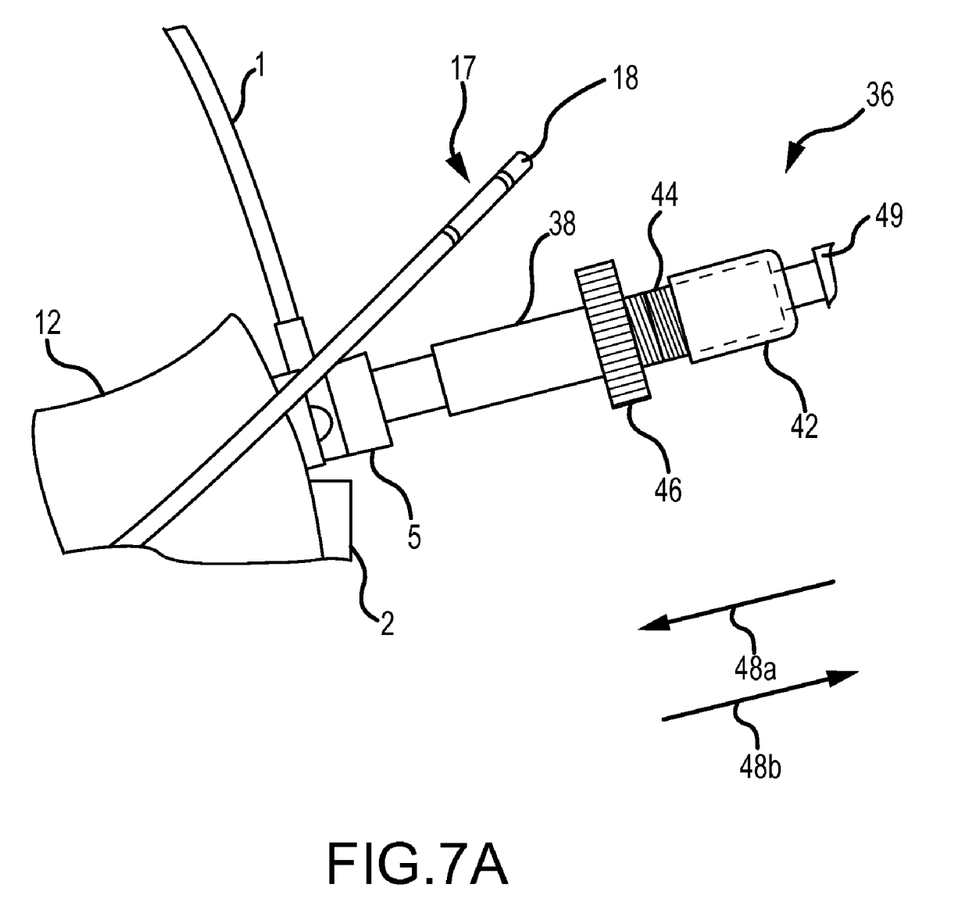
FIG. 7a-b are side views of the needle deployment system shown in FIG. 6 illustrating exemplary use to control positioning of the needle.

The plunger 42 may be spring-loaded. It is noted that the spring is internal and therefore not shown in FIG. 6 for sake of clarity. However, the spring acts to bias the plunger in a fully extended or pulled back position (e.g., as shown in FIG. 7a). A force must be applied to the plunger 42 (e.g., by the user depressing the plunger 42) in order to move the plunger 42, and hence the needle 20 (e.g., into the tissue). Accordingly, the plunger 42 is automatically returned to its fully extended or pulled-back position when the plunger 42 is released (e.g., to retract the needle from the tissue). This may help ensure that the user does not leave the needle 20 exposed from the catheter shaft during removal of the catheter system from the patient's body. This may also help ensure that the needle 20 is not accidentally deployed during placement of the catheter system in the patient's body (doing so could cause unintended damage to tissue or other parts of the patient's body).

Other embodiments of needle deployment systems are also contemplated and are not limited to the specific implementation shown in FIG. 6. For example, different mechanisms for controlling the distance 47 between the plunger 42 and the depth control ring 46 to control the distance 47 that the needle 20 can travel may be implemented. Likewise, positioning of the depth control ring 46 is not limited to threads and other locking mechanisms may also be employed.

Figure 7B:
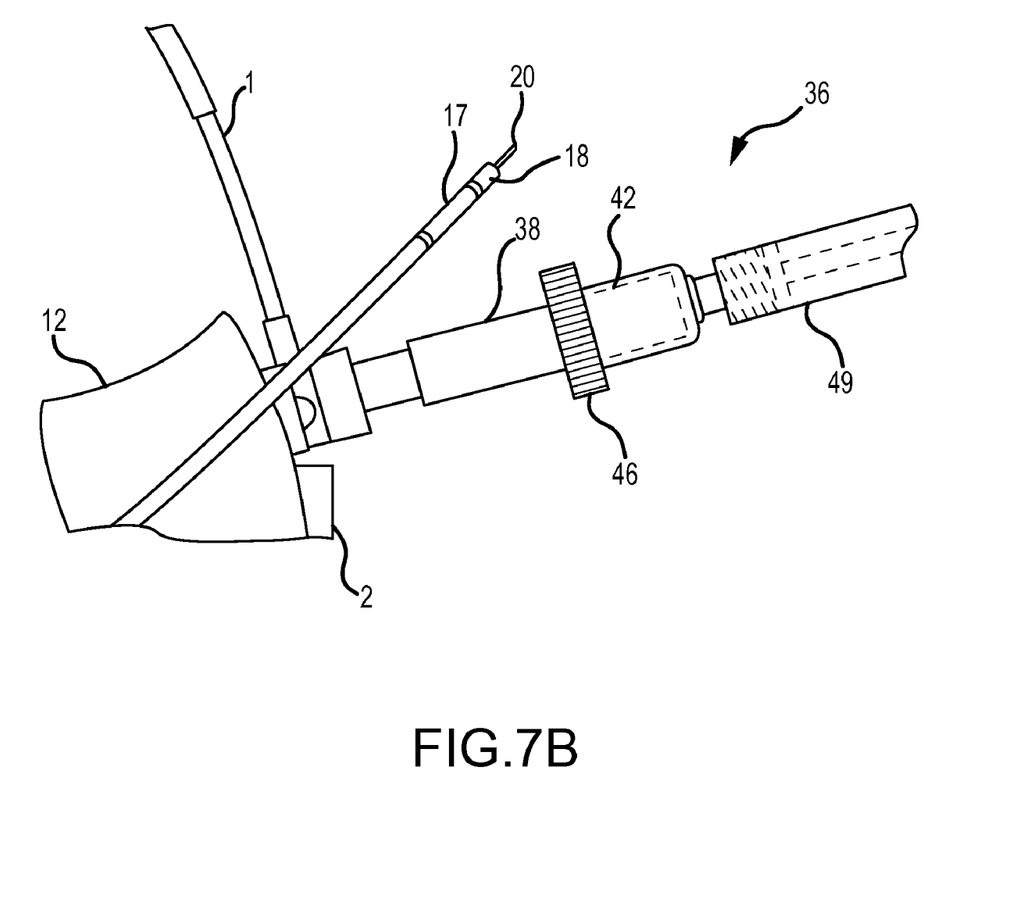

FIG. 7a-b are side views of the needle deployment system 36 shown in FIG. 6 illustrating exemplary use to control movement of the needle 20 (see FIG. 7b). In these figures, the needle deployment system 36 is shown as it may be connected to port 5 of the handle 12 of the catheter system 10 (e.g., refer to FIG. 1). In addition, the distal end portion 17 of the catheter system 10 is shown as it may be wrapped back around toward the handle 12 for purposes of illustration to show movement of the needle 20 in response to movement of the plunger 42 (e.g., compare position of needle 20 between FIG. 7a and FIG. 7b).

In FIG. 7a, the plunger 42 is shown in its fully retracted or pulled-back position. The depth control ring 46 is set at a predetermined distance (i.e., distance 47 in FIG. 6 corresponding to the desired movement of the needle 20). The needle 20 is retracted within the sheath 18 as it cannot be seen at distal end portion 17 in FIG. 7a. Once positioned in the heart, the plunger 42 may be pushed or otherwise moved toward the depth control ring 46 (e.g., in the direction illustrated by arrow 48a) until the plunger 42 abuts against the depth control ring 46.

Movement of the plunger 42 directly translates to movement of the needle 20, and the needle 20 can be seen in FIG. 7b extending out from the sheath 18 at distal end portion 17 of the catheter system 10. A syringe 49 may be connected to the needle deployment system 36 as best seen in FIG. 7B for fluid delivery (e.g., biologic or chemical agents, or other therapeutic fluid). The biologic or chemical agents, or other therapeutic fluid is injected using syringe 49 and travels the length of the catheter for injection by needle 20 into the tissue.

After injection of the fluid, the plunger 42 may be released. Spring-action may automatically return the plunger 42 (e.g., in the direction illustrated by arrow 48b in FIG. 7a) to a fully retracted or pulled-back position. The needle 20 also retracts and can be safely removed from the patients body by withdrawing the catheter system 10 in a conventional manner.

Figure 8:
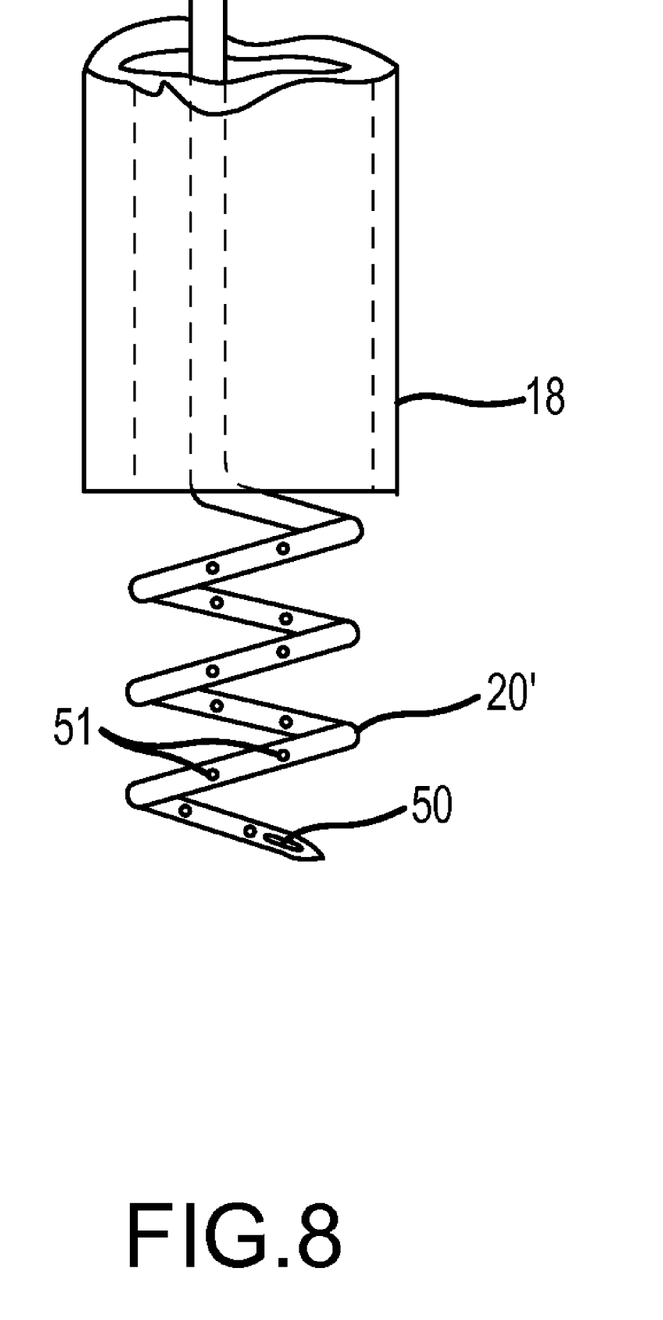
FIG. 8 is a perspective view of a needle showing another exemplary embodiment of an anchor for securing the catheter system to a tissue.

FIG. 8 is a perspective view of a needle 20' showing another exemplary embodiment of an anchor for securing the needle 20' to a tissue 25. In this embodiment, the anchor again comprises a helical shaped needle. However, instead of the anchor being formed as part of or connected to the sheath 18 (as in the embodiment shown in FIG. 5a-c), the anchor is formed as part of the needle 20'. The needle 20' may have one or more fluid ports (e.g., ports 50, 51) so that the needle 20' serves both as the anchor and the means for delivery of biologic or chemical agents, or other therapeutic fluid to the tissue.

Figure 9A:
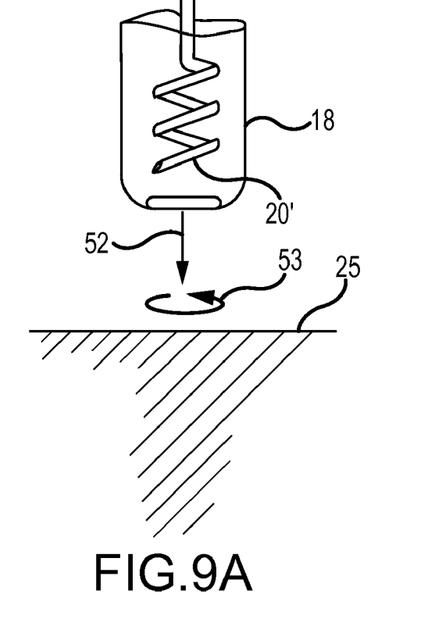
FIG. 9a-c are side views of the needle shown in FIG. 8 illustrating exemplary use of the anchor.
Figure 9B:
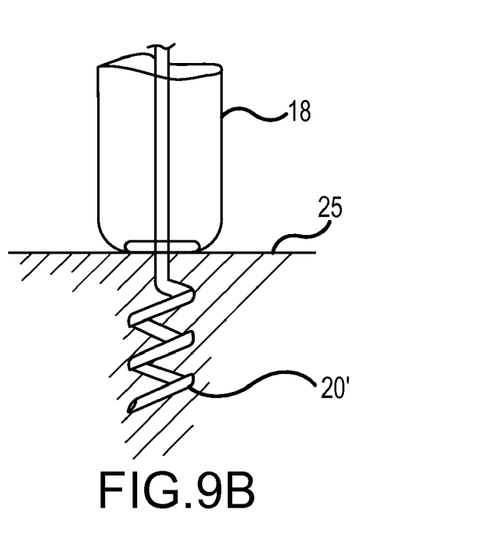
Figure 9C:
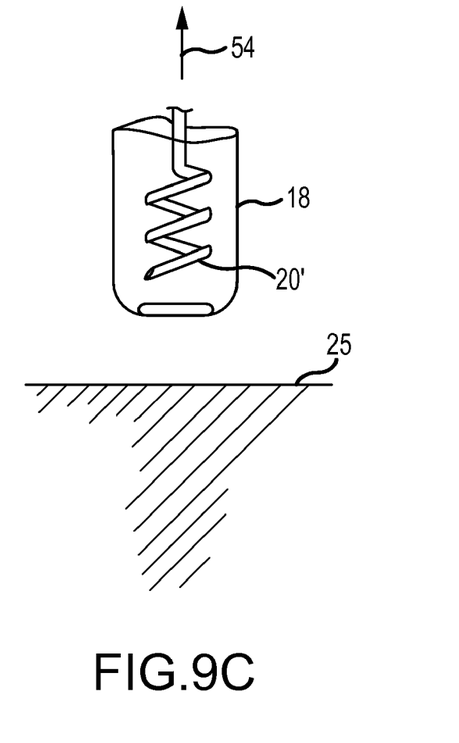

FIG. 9a-c are side views of the needle 20' shown in FIG. 8 illustrating exemplary use of the anchor to secure the needle 20' to the tissue 25. During use, the guiding introducer (refer to FIG. 1 and description thereof, not shown in FIG. 9a-c for sake of clarity) may be moved (e.g., in the direction illustrated by arrow 52 in FIG. 9a) so that the distal end portion of sheath 18 is positioned adjacent the tissue 25. The needle 20' can then be advanced by rotating it (e.g., in the direction illustrated by arrow 53 in FIG. 9a) so that the needle 20' engages the tissue 25 and secures the needle 20' to the tissue 25 as shown in FIG. 9b. The needle 20' may then be used for delivery of biologic or chemical agents, or other therapeutic fluid. After delivery, the needle 20' may be rotated opposite to the direction illustrated by arrow 53 in FIG. 9a to release needle 20' from the tissue 25. The needle 20' can then be retracted back into the sheath 18 (e.g., in the direction illustrated by arrow 54 shown in FIG. 9c) and removed from the patient's body in a conventional manner.

It is noted that the various embodiments of catheter system 10 described above with reference to the figures may also be implemented with a wide variety of different sensing means. These sensing means enable the catheter system 10 to be implemented for tissue contact assessment during the procedures, including contact of the sheath and other distal-end components of the catheter system 10 with the tissue 25, and depth of the needle 25 within the tissue 25.

In an exemplary embodiment the catheter system 10 may include one or more piezoelectric sensor embedded in the sheath 18. The piezoelectric sensor generates electric signals in response to stresses caused by contact with the tissue. Radiopaque sensors (illustrated by bands 55 shown in FIG. 1) may also be used. Still other exemplary sensing devices may include pressure, thermistor, thermocouple, or ultrasound sensors. In addition, more than one sensor or type of sensor may be implemented to provide additional feedback to the user. In any event, when the sheath 18 is positioned in contact with and/or moved over a tissue, the sensor generates an electrical signal corresponding to stress caused by this contact and/or movement.

In another exemplary embodiment, the needle may be coated with conductive material, and/or conductive fluids may flow through the sheath 18 (e.g., through interstitial spaces shown in FIG. 2b and FIG. 2c) and around the needle. The corresponding electrical signals may be used to indicate depth of the needle in the tissue. For example, impedance measurements may be correlated to tissue depth assessment.

Electrical wiring (not shown) may also extend through the lumen of the catheter system 10 to enable these sensors. The electrical wiring may convey electrical signals from the sensor(s) to a data acquisition/processing/output device (also not shown), such as, e.g., an echocardiogram (ECG) device. Alternatively, a wireless connection may be implemented, e.g., by providing a transmitter in the catheter and a receiver in association with the data acquisition/processing/output device. Accordingly, the electrical signals from the sensor(s) may be viewed by the user, e.g., as output on an electrical monitoring device. The resulting electrical signal may be processed and/or otherwise output for the user so that the user is able to assess tissue contact by the catheter system 10.

It is noted that any suitable analog and/or digital device may be implemented for outputting the electrical signals generated by the sensor(s) to a user. In addition, the electrical signals may be further characterized using a suitable processing device such as, but not limited to, a desktop or laptop computer. Such processing device may be implemented to receive the voltage signal generated by the contact assessment sensor(s) and convert it to a corresponding contact condition and output for the user, e.g., at a display device, an audio signal, or tactile feedback or vibrations on the handle of the catheter. In any event, circuitry for conveying output of the piezoelectric sensor to a user in one form or another may be readily provided by those having ordinary skill in the electronics arts after becoming familiar with the teachings herein.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. In addition, various combinations of the embodiments shown are also contemplated even if not particularly described. Changes in detail or structure, such as but not limited to combinations of various aspects of the disclosed embodiments, may be made without departing from the spirit of the invention as defined in the appended claims.

What is claimed is:

1. A tissue anchoring catheter comprising:
an outer catheter shaft connected to a catheter handle;
a delivery sheath provided within the outer catheter shaft, the delivery sheath housing a needle; and
at least one anchor operatively associated with the delivery sheath, the at least one anchor operable at the catheter handle to secure the delivery sheath to tissue for conveying biologic or chemical agents, or other therapeutic fluid from the needle to the tissue;
at least one window formed in the needle, the window retaining the anchor within the needle until the needle is inserted into the tissue, the window releasing the anchor to expand within the tissue after the needle is inserted into the tissue; and
a needle deployment system near the catheter handle, the needle deployment system including an adjustable depth control ring and a plunger, the needle deployment system ejecting the needle from the delivery sheath as the plunger is moved toward the depth control ring, and the depth control ring stopping movement of the plunger at a preset depth.

2. The tissue anchoring catheter of claim 1, wherein the anchor includes at least one barb.

3. The tissue anchoring catheter of claim 2, wherein the at least one barb deploys automatically as the needle advances out of the delivery sheath.

4. The tissue anchoring catheter of claim 2, wherein the at least one barb retracts automatically as the needle is pulled into the delivery sheath.

5. The tissue anchoring catheter of claim 1, wherein the plunger is spring-biased to automatically retract the needle within the delivery sheath when the plunger is released.

6. The tissue anchoring catheter of claim 1, wherein the tissue is tissue of an internal organ.

7. The tissue anchoring catheter of claim 1, further comprising a support structure within the delivery sheath, the support structure providing mechanical support for the needle.

8. The tissue anchoring catheter of claim 7, wherein the support structure is substantially star-shaped.

9. The tissue anchoring catheter of claim 7, wherein the support structure is substantially hub-shaped.

10. The tissue anchoring catheter of claim 7, wherein the support structure includes interstitial spaces forming a fluid delivery conduit between the delivery sheath and the needle.

11. The tissue anchoring catheter of claim 1, further comprising at least one sensor at a distal end of the outer catheter shaft, the at least one sensor responsive to contact of the outer catheter shaft with tissue, the at least one sensor generating electrical signals corresponding to the amount of contact with the tissue.

12. The tissue anchoring catheter of claim 1, further comprising at least one sensor at a tip portion of the outer catheter shaft, the at least sensor responsive to contact of the outer catheter shaft with tissue, the at least one sensor generating electrical signals corresponding to the amount of contact with the tissue.

13. The tissue anchoring catheter of claim 1, wherein the needle is conductive, the conductive needle sensing needle contact with the tissue.

14. A method comprising:
guiding a delivery sheath adjacent tissue inside a patient's body;

anchoring the delivery sheath to the tissue;
deploying a needle from within the delivery sheath;
wherein anchoring the delivery sheath to the tissue is after advancing an outer portion of the needle into the tissue occurs, and wherein deploying an inner portion of the needle is after anchoring the delivery sheath to the tissue; and
conveying biologic or chemical agents, or other therapeutic fluid from the needle to the tissue.

15. The method of claim 14, further comprising assessing depth of the needle within the tissue.

16. The method of claim 14, further comprising deploying at least one barb as the needle advances out of the delivery sheath to anchor the delivery sheath to the tissue.

17. The method of claim 16, further comprising retracting the at least one barb as the needle is pulled back into the delivery sheath.

18. The method of claim 14, further comprising ejecting the needle from the delivery sheath as a plunger is moved on a catheter handle, and stopping movement of the plunger at a preset depth.

19. The method of claim 18, further comprising automatically retracting the needle within the delivery sheath when the plunger is released.

20. A system comprising:
means for guiding a delivery sheath adjacent tissue inside a patient's body;
means for anchoring the delivery sheath to the tissue; and
means for deploying a needle from within the delivery sheath for conveying biologic or chemical agents, or other therapeutic fluid from the needle to the tissue;
wherein the means for anchoring the delivery sheath to the tissue secures the delivery sheath to the tissue by advancing the needle in a first direction into the tissue, the means for anchoring the delivery sheath to the tissue releasing the delivery sheath from the tissue by further advancing the needle in the first direction before removing the needle from the tissue in a second direction;
plunger means for ejecting the needle from the delivery sheath;
means for stopping movement of the plunger means at a depth; and
means for automatically retracting the needle within the delivery sheath if the plunger means is released.

21. The system of claim 20, further comprising:
means for automatically deploying an anchor as the needle advances out of the delivery sheath; and
means for retracting the anchor as the needle is pulled back into the delivery sheath.

22. A tissue anchoring catheter comprising:
an outer catheter shaft connected to a catheter handle;
a delivery sheath provided within the outer catheter shaft; and
an anchor operatively associated with the delivery sheath, the anchor having at least one fluid delivery port, the anchor operable at the catheter handle to both secure the delivery sheath to tissue and convey biologic or chemical agents, or other therapeutic fluid to the tissue;
a needle having at least one window formed therein, the anchor is retained within the needle behind the window until the needle is inserted into the tissue, the anchor released from the window after the needle is inserted into the tissue.

23. The tissue anchoring catheter of claim 1, wherein the needle is further advanced into the tissue to release the anchor from the tissue before withdrawing the needle from the tissue.

24. The method of claim 14, further comprising continuing advancing the inner portion of the needle into the tissue to release the anchor from the tissue before withdrawing the needle from the tissue.

25. The tissue anchoring catheter of claim 22, wherein the anchor expands within the tissue after the needle is inserted into the tissue.

26. A tissue anchoring catheter comprising:
an outer catheter shaft connected to a catheter handle;
a delivery sheath provided within the outer catheter shaft, the delivery sheath housing a needle; and
at least one anchor operatively associated with the delivery sheath, the at least one anchor operable at the catheter handle to secure the delivery sheath to tissue for conveying biologic or chemical agents, or other therapeutic fluid from the needle to the tissue;
at least one window formed in the needle, the window retaining the anchor within the needle until the needle is inserted into the tissue, the window releasing the anchor to expand within the tissue after the needle is inserted into the tissue; and
at least one sensor at a distal end of the outer catheter shaft, the at least one sensor responsive to contact of the outer catheter shaft with tissue, the at least one sensor generating electrical signals corresponding to the amount of contact with the tissue.

27. A tissue anchoring catheter comprising:
an outer catheter shaft connected to a catheter handle;
a delivery sheath provided within the outer catheter shaft, the delivery sheath housing a needle; and
at least one anchor operatively associated with the delivery sheath, the at least one anchor operable at the catheter handle to secure the delivery sheath to tissue for conveying biologic or chemical agents, or other therapeutic fluid from the needle to the tissue;
at least one window formed in the needle, the window retaining the anchor within the needle until the needle is inserted into the tissue, the window releasing the anchor to expand within the tissue after the needle is inserted into the tissue; and
at least one sensor at a tip portion of the outer catheter shaft, the at least sensor responsive to contact of the outer catheter shaft with tissue, the at least one sensor generating electrical signals corresponding to the amount of contact with the tissue.

28. A tissue anchoring catheter comprising:
an outer catheter shaft connected to a catheter handle;
a delivery sheath provided within the outer catheter shaft, the delivery sheath housing a needle, wherein the needle is conductive, the conductive needle sensing needle contact with the tissue; and
at least one anchor operatively associated with the delivery sheath, the at least one anchor operable at the catheter handle to secure the delivery sheath to tissue for conveying biologic or chemical agents, or other therapeutic fluid from the needle to the tissue; and
at least one window formed in the needle, the window retaining the anchor within the needle until the needle is inserted into the tissue, the window releasing the anchor to expand within the tissue after the needle is inserted into the tissue.

29. A tissue anchoring catheter comprising:
an outer catheter shaft connected to a catheter handle;
a delivery sheath provided within the outer catheter shaft, the delivery sheath housing a needle; and
at least one anchor operatively associated with the delivery sheath, the at least one anchor operable at the catheter handle to secure the delivery sheath to tissue for conveying biologic or chemical agents, or other therapeutic fluid from the needle to the tissue;

at least one window formed in the needle, the window retaining the anchor within the needle until the needle is inserted into the tissue, the window releasing the anchor to expand within the tissue after the needle is inserted into the tissue; and a support structure within the delivery sheath, the support structure providing mechanical support for the needle, wherein the support structure is substantially star-shaped.

30. A tissue anchoring catheter comprising:

an outer catheter shaft connected to a catheter handle;

a delivery sheath provided within the outer catheter shaft, the delivery sheath housing a needle; and at least one anchor operatively associated with the delivery sheath, the at least one anchor operable at the catheter handle to secure the delivery sheath to tissue for conveying biologic or chemical agents, or other therapeutic fluid from the needle to the tissue;

at least one window formed in the needle, the window retaining the anchor within the needle until the needle is inserted into the tissue, the window releasing the anchor to expand within the tissue after the needle is inserted into the tissue; and a support structure within the delivery sheath, the support structure providing mechanical support for the needle, wherein the support structure includes interstitial spaces forming a fluid delivery conduit between the delivery sheath and the needle.

* * * * *